(12) United States Patent
Ueda (10) Patent No.: US 7,330,751 B2
(45) Date of Patent: Feb. 12, 2008

(54) HEARTBEAT DETECTION DEVICE (75) Inventor: Takashi Ueda, Izumi (JP)

(73) Assignee: Cateye Co., Ltd., Osaka (JP)

( * ) Notice: Subject to any disclaimer, the term of this patent is extended or adjusted under 35 U.S.C. 154(b) by 365 days.

(21) Appl. No.: 10/918,886

(22) Filed: Aug. 16, 2004

(65) Prior Publication Data
US 2005/0043641 A1 Feb. 24, 2005

(30) Foreign Application Priority Data
Aug. 22, 2003 (JP) .............................. 2003-298677

(51) Int. Cl.
*A61B 5/0416* (2006.01)

(52) U.S. Cl. ..................... 600/509; 600/382; 600/388; 600/390

(58) Field of Classification Search ................ 600/372, 600/382, 384, 386, 388, 389, 390, 393, 394, 600/519, 520, 502, 375, 547; 607/72, 115, 607/142, 149
See application file for complete search history.

(56) References Cited

U.S. PATENT DOCUMENTS

| | | | | |
|---|---|---|---|---|
| 3,865,101 A * | 2/1975 | Saper et al. ................ 600/508 |
| 4,608,987 A | 9/1986 | Mills ........................... 128/639 |
| 4,662,378 A * | 5/1987 | Thomis ....................... 600/382 |
| 4,974,956 A * | 12/1990 | Gill ............................. 351/156 |
| 5,169,380 A * | 12/1992 | Brennan ...................... 600/26 |
| 5,491,474 A | 2/1996 | Suni et al. ............. 340/870.31 |
| 6,259,939 B1 * | 7/2001 | Rogel .......................... 600/390 |
| 6,277,080 B1 | 8/2001 | Nissila et al. ............... 600/508 |
| 6,400,975 B1 * | 6/2002 | McFee ........................ 600/372 |
| 6,431,705 B1 * | 8/2002 | Linden ........................ 351/158 |
| D519,636 S * | 4/2006 | Okuda et al. .............. D24/168 |
| 2004/0138573 A1 * | 7/2004 | Chen .......................... 600/509 |

FOREIGN PATENT DOCUMENTS

| | | |
|---|---|---|
| DE | 20019830 | 2/2001 |
| JP | 6070897 | 3/1994 |
| WO | WO 02/30279 | * 4/2002 |

* cited by examiner

*Primary Examiner*—Carl Layno
*Assistant Examiner*—Eugene Wu
(74) *Attorney, Agent, or Firm*—Olson & Cepuritis, Ltd.

(57) ABSTRACT

A heartbeat detection device includes a pair of electrode units, a transmitting unit and a receiving unit. The transmitting unit is electrically connected to the paired electrode units each by respective wires. The paired electrode units each include an electrode body and a hook sandwiching a bottom part of a garment for example on a body for holding the electrode units on respective predetermined parts of the body. The hook is formed on the front side of the electrode unit. The transmitting unit includes a transmitting-unit body and a hook sandwiching an upper part of the garment for holding the transmitting unit on the garment. The hook is formed on the rear side of the transmitting unit. The lightweight heartbeat detection device is thus achieved that can ensure electrical contact between the electrode units and respective predetermined parts of the chest without causing a feeling of tightness.

6 Claims, 9 Drawing Sheets

HEARTBEAT DETECTION DEVICE

BACKGROUND OF THE INVENTION

1. Field of the Invention

The present invention relates to heartbeat detection devices. In particular, the present invention relates to an heartbeat detection device transmitting, by radio, to a separate receiver, a signal concerning heartbeat detected by electrodes.

2. Description of the Background Art

U.S. Pat. No. 5,491,474 for example discloses a heartbeat detection device transmitting, by radio, to a receiver, information about an electric potential detected by electrode(s) in electrical contact with the chest of a subject, the information being transmitted in the form of heartbeat signals, for display and storage for example of the transmitted data.

Figure 11:
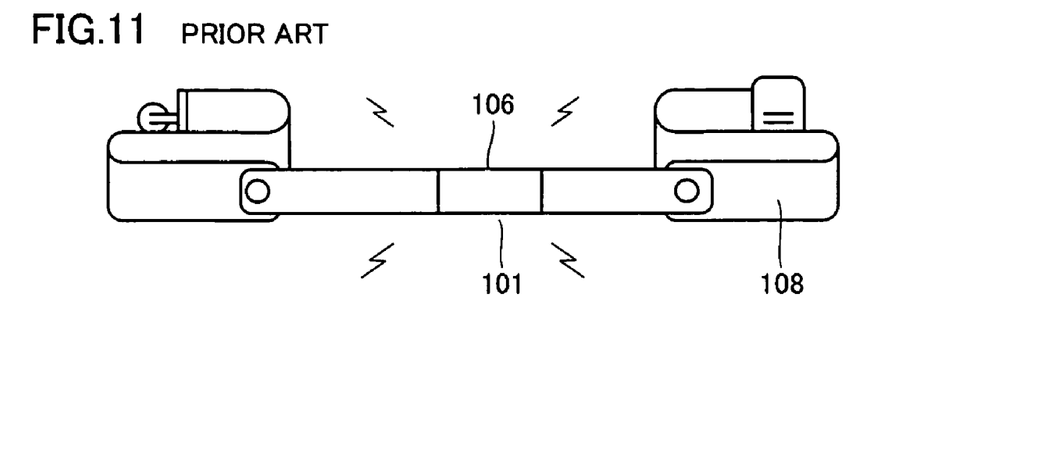
FIG. 11 is a perspective view of a conventional heartbeat detection device.
Figure 12:
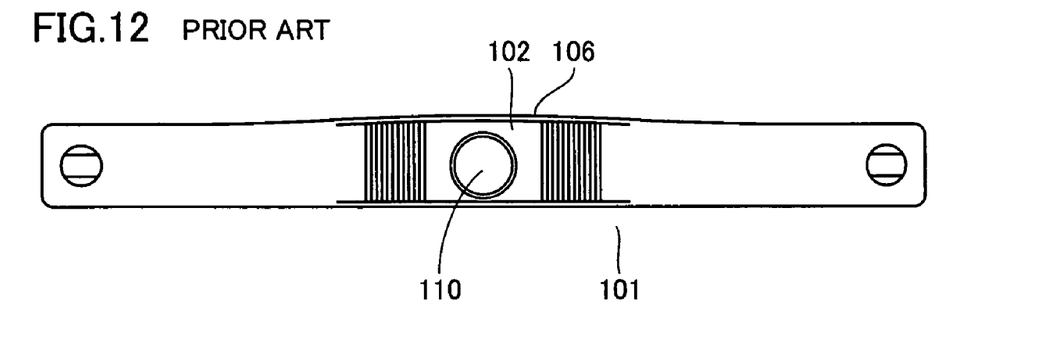
FIG. 12 is a partial enlarged front view of the heartbeat detection device shown in FIG. 11.

One of conventional heartbeat detection devices, disclosed in the above-described U.S. patent, is described now. As shown in FIGS. 11 and 12, a heartbeat detection device 101 includes a predetermined casing 106 having electrodes and a transmitter, and a belt 108 for fastening purpose is attached to the longitudinal ends of casing 106 so that casing 106 can be mounted on the chest.

Figure 13:
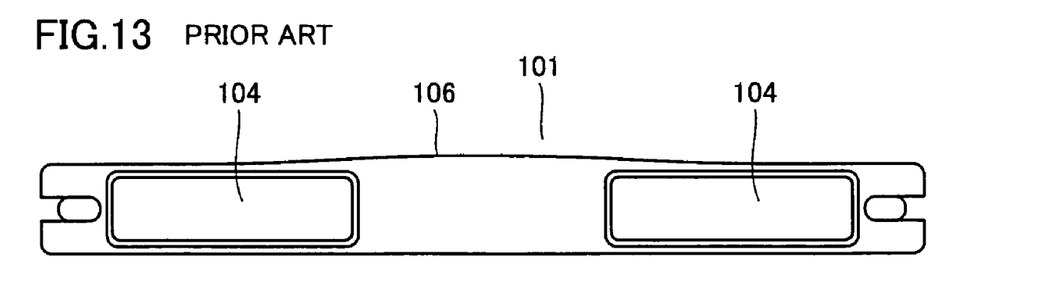
FIG. 13 is another partial enlarged front view of the heartbeat detection device shown in FIG. 11.

Casing 106 is plastic in nature. As shown in FIG. 13, within casing 106 mounted on and accordingly facing the chest, two electrodes 104 in electrical contact with the chest are provided with a certain distance therebetween. Between these two electrodes 104, as shown in FIG. 12, a transmitter 102 is provided that is electrically connected to electrodes 104 for transmitting signals detected by electrodes 104 to a receiver (not shown).

Belt 108 is fastened to allow casing 106 which is now a part of belt 108 to be brought into intimate contact with the chest, so that two electrodes 104 electrically contact two different areas on the chest to detect the potential difference therebetween. The detected potential difference is provided to transmitter 102 and transmitter 102 then transmits to the receiver the potential difference in the form of signals concerning heartbeat.

The above-described conventional heartbeat detection device 101, however, has some problems. Specifically, since two electrodes 104 as well as transmitter 102 relatively heavier than electrodes 104 are included in one casing 106, this casing 106 is likely to vibrate or swing as the body of the subject with the detection device mounted thereon moves. Swinging of casing 106 eventually causes electrodes 104 to swing together, leading to a problem that accurate signals concerning heartbeat cannot be detected due to changes in position of contact of electrodes 104.

Further, the plasticity of casing 106 is not enough to ensure the contact of electrodes 104 with predetermined areas. In order to surely bring electrodes 104 into contact with predetermined areas, belt 108 must be fastened to a considerable degree so that casing 106 is hardly pressed against the chest, leading to a problem that the subject could feel tight.

SUMMARY OF THE INVENTION

The present invention has been made to solve the problems described above. An object of the present invention is to provide a heartbeat detection device having an electrode unit that can surely be brought into electrical contact with a predetermined part of the chest without causing a feeling of tightness or pressure, and achieving lightweight.

A heartbeat detection device according to the present invention includes a pair of electrode units, a first clipping unit, a transmitting unit, a wire, and a receiving unit. The paired electrode units electrically contact predetermined parts respectively of a body for detecting an electric potential concerning heartbeat. The first clipping unit is provided to each of the paired electrode units for sandwiching an article worn by the body for holding the paired electrode units on respective predetermined parts of the body. The transmitting unit transmits, as a heartbeat signal, information about the electric potential detected by the paired electrode units. The wire connects the paired electrode units each with the transmitting unit. The receiving unit receives the heartbeat signal transmitted from the transmitting unit.

With the above-described structure, the first clipping unit is used for sandwiching the article worn by the body to hold the paired electrode units at predetermined positions on the chest without causing a feeling of tightness. Further, the transmitting unit and each of the electrode units are connected by the wire so that the transmitting unit and the electrode units each are separated. Therefore, even if the transmitting unit which is relatively heavier than the electrode units moves, the electrode units do not follow the movement of the transmitting unit and thus the contact between the paired electrode units and predetermined positions respectively on the chest can be ensured. In addition, it is unnecessary to provide the electrode units and the transmitting unit in one casing, so that the heartbeat detection device can be reduced in weight.

Preferably, for the purpose of sandwiching the article worn by the body, the paired electrode units each include an electrode body electrically contacting a predetermined part of the body and a hook provided on a side of the electrode unit that is opposite to a side thereof which faces the body and on which the electrode body is provided, and the electrode body and the hook serve as the first clipping unit for clipping from underneath the article worn by the body.

When the article worn by the body is such a garment as sports brassiere, a bottom part of the sports brassiere can be sandwiched by the first clipping unit for holding the electrode units on the sports brassiere.

Preferably, the heartbeat detection device may further include an attachment belt serving as the article worn by the body, and a hook-inserted portion provided in the attachment belt for receiving the hook of the first clipping unit to catch the paired electrode units each by the attachment belt.

In this case, the electrode units are attached to the attachment belt by sandwiching a bottom part of the attachment belt by the first clipping unit, inserting the hook into the hook-inserted portion and then winding the attachment belt around the chest. Then, if a subject wears such a garment except for the sports brassiere as sports shirts, the electrode units can readily be held on predetermined parts respectively of the body without causing a feeling of tightness.

Preferably, the paired electrode units each include projections provided on a side of the electrode unit that faces the body.

Thus, slipping of the electrode units along the body can be prevented, and thus contact between the electrode units and predetermined positions on the chest can be ensured.

Preferably, the transmitting unit includes a second clipping unit for clipping from above the article worn by the body.

An upper part of the article worn by the body can thus be sandwiched by the second clipping unit so that the transmitting unit can easily be held on the article.

Preferably, the second clipping unit has a function of catching a ring-shaped cord suspended from neck.

Accordingly, when the transmitting unit relatively heavier than the electrode units moves, the transmitting unit can be prevented from being disengaged and dropping from the article worn by the body.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

First Embodiment

Figure 1:
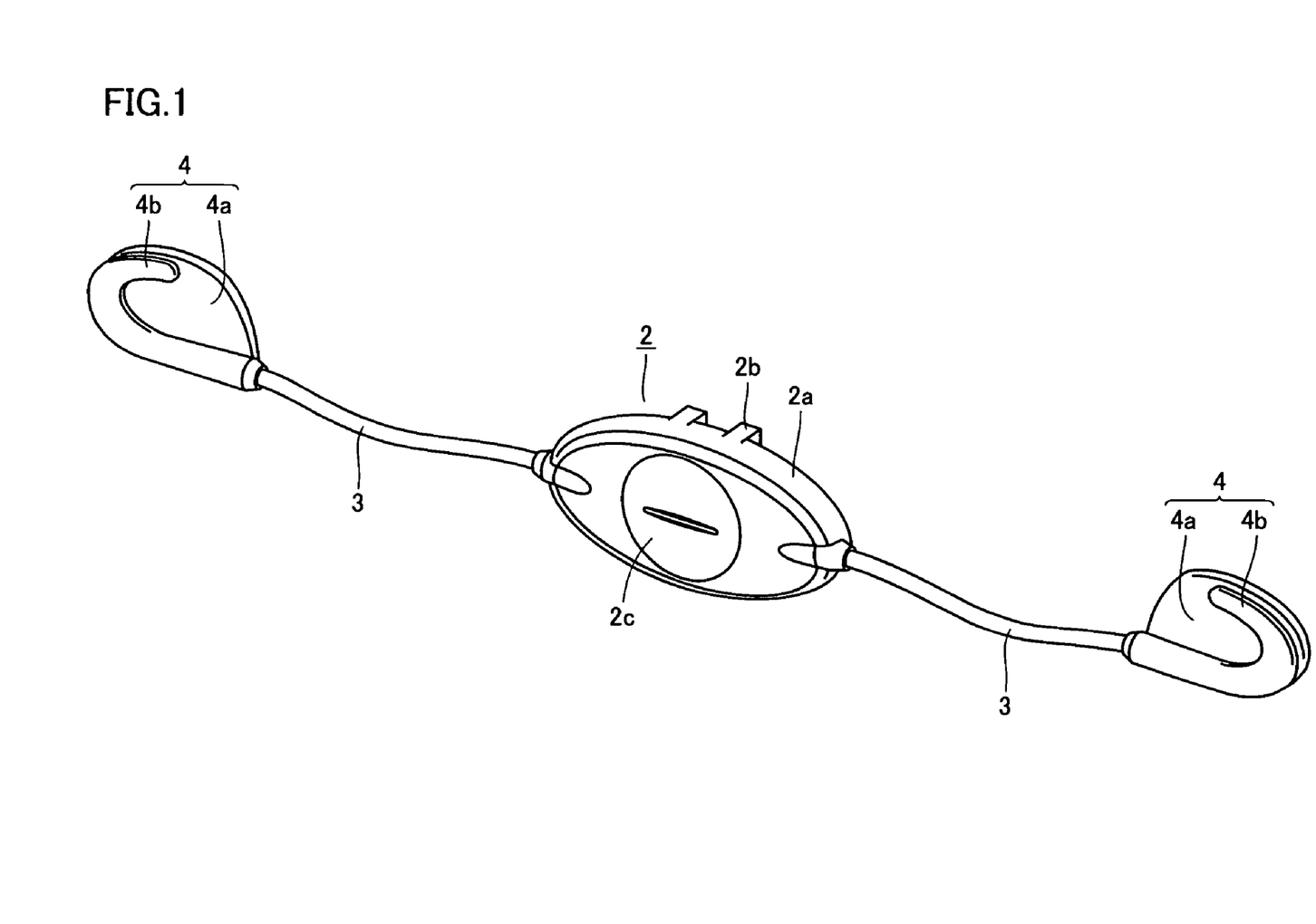
FIG. 1 is a perspective view of a heartbeat detection device according to a first embodiment of the present invention.
Figure 2:
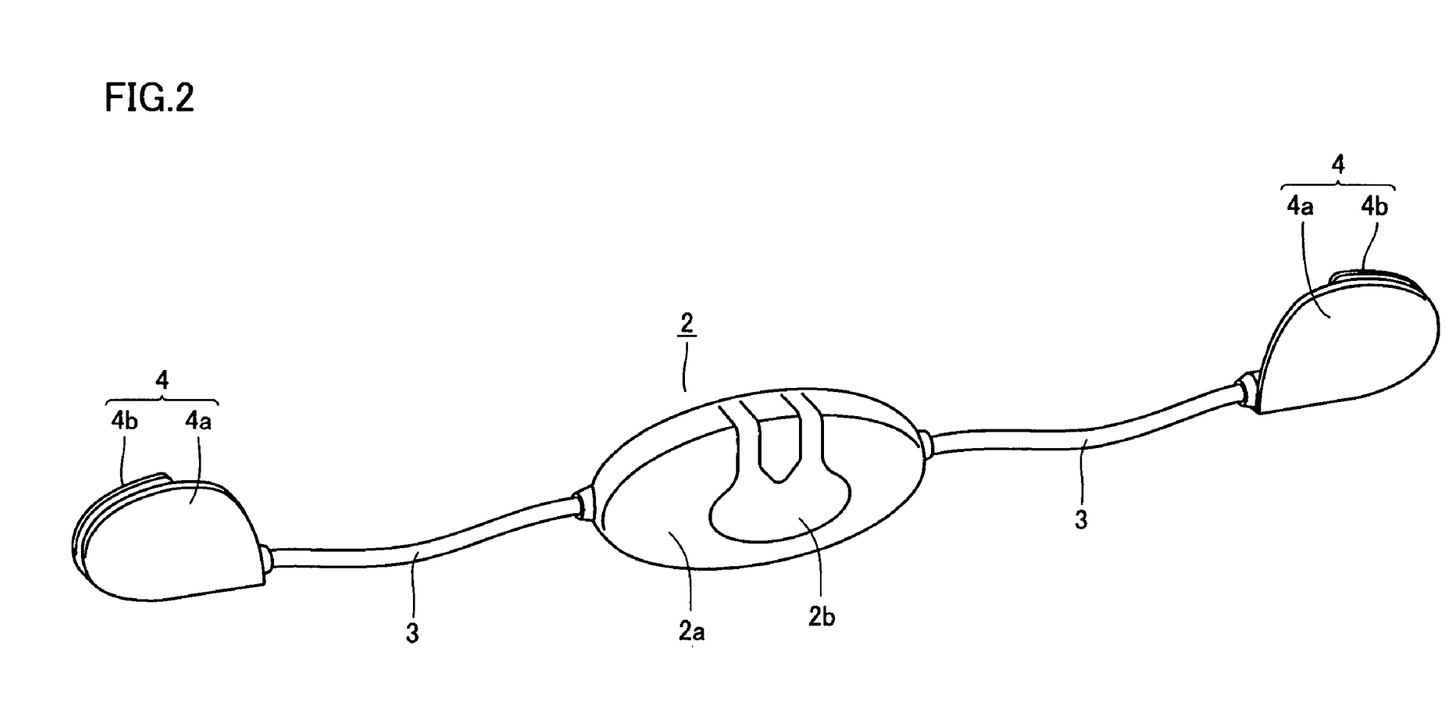
FIG. 2 is another perspective view of the heartbeat detection device of the first embodiment shown in FIG. 1.

A heartbeat detection device according to a first embodiment of the present invention is hereinafter described. Referring to FIGS. 1 and 2, heartbeat detection device 1 includes a pair of electrode units 4, a transmitting unit 2 and a receiving unit 6 (see FIG. 7). Paired electrode units 4 detect an electric potential concerning heartbeat. Transmitting unit 2 is electrically connected by a wire (cord) 3 to each of paired electrode units 4 to transmit, to receiving unit 6 mounted on right or left arm for example, information about the potential detected by paired electrode units 4 in the form of heartbeat signals.

Figure 3:
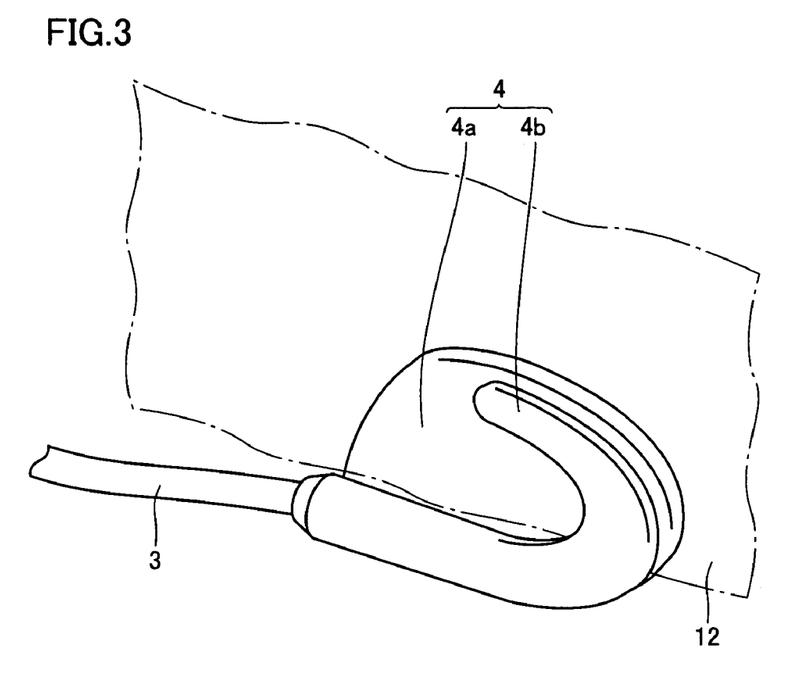
FIG. 3 is a partial perspective view illustrating an electrode unit of the heartbeat detection device of the first embodiment shown in FIG. 1.

Each of paired electrode units 4 includes, as shown in FIG. 3, an electrode body 4a and a hook 4b that serve as a first clipping unit sandwiching a bottom part of a garment 12 for example worn by a subject, for holding electrode unit 4 at a predetermined part of the body of the subject. Hook 4b is provided on the "front side" of electrode unit 4 with respect to the "rear side" thereof that faces the body of the subject, and is curved upward from the bottom of electrode unit 4 ("front side" and "rear side" are hereinafter used in the above-described meaning).

Figure 4:
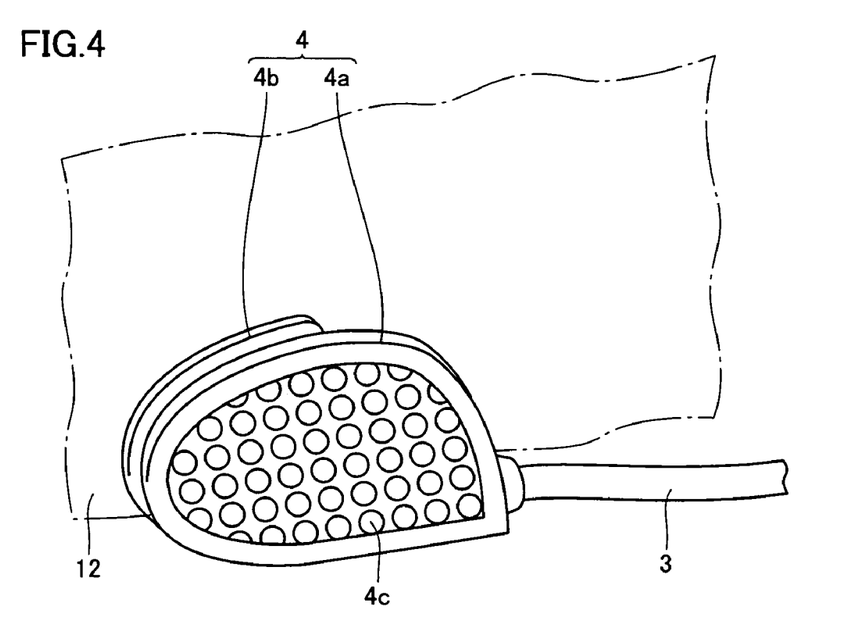
FIG. 4 is another partial perspective view illustrating the electrode unit of the heartbeat detection device of the first embodiment shown in FIG. 1.
Figure 5:
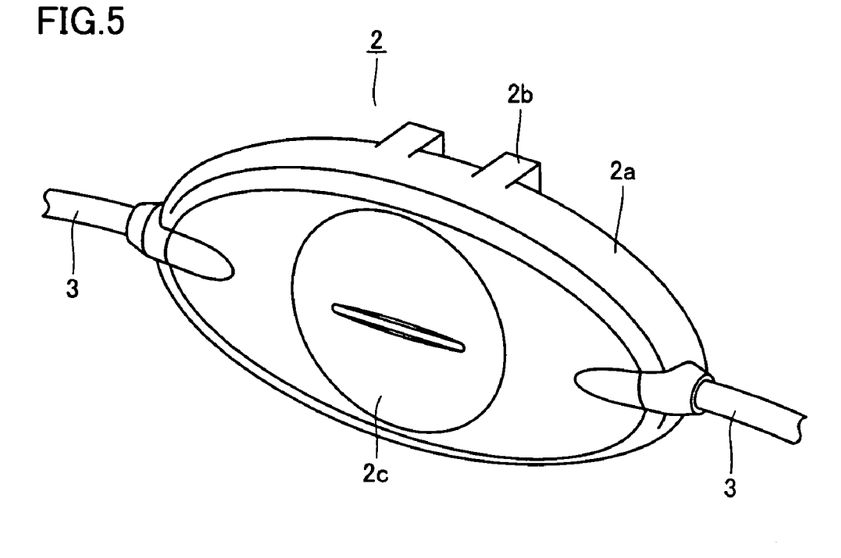
FIG. 5 is a partial perspective view illustrating a transmitting unit of the heartbeat detection device of the first embodiment shown in FIG. 1.
Figure 6:
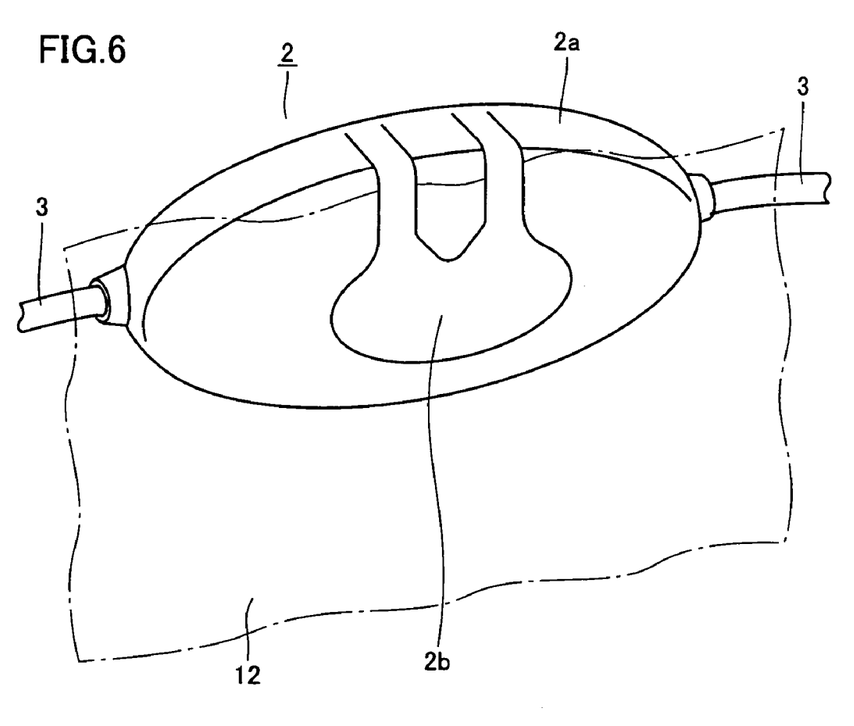
FIG. 6 is another partial perspective view illustrating the transmitting unit of the heartbeat detection device of the first embodiment shown in FIG. 1.

As shown in FIG. 4, on the rear side of paired electrode units 4 each, a plurality of projections 4c are provided for ensuring the contact between electrode unit 4 and the body. Here, instead of the dome-shaped projections as shown in FIG. 4, wavelike projections for example may be provided. The wavelike projections provide a relatively better feel of contact for the skin and easy washing of the surface of the projections. Referring to FIGS. 5 and 6, transmitting unit 2 has a transmitting-unit body 2a and a hook 2b that serve as a second clipping unit sandwiching an upper part of garment 12 for example worn by the subject for holding transmitting unit 2 on garment 12. Hook 2b is provided to extend downward from the top on the rear side of transmitting unit 2.

On the front side of transmitting unit 2, a lid 2c is provided for replacement of a lithium battery for example. Hook 2b has an additional function of catching a ring-shaped cord suspended from the neck as discussed hereinlater.

In particular, the above-described heartbeat detection device has paired electrode units 4 each provided with electrode body 4a and hook 4b so that a bottom part of a garment for example worn by the subject can be sandwiched therebetween as well as transmitting unit 2 provided with transmitting-unit body 2a and hook 2b so that an upper part of the garment can be sandwiched therebetween.

Figure 7:
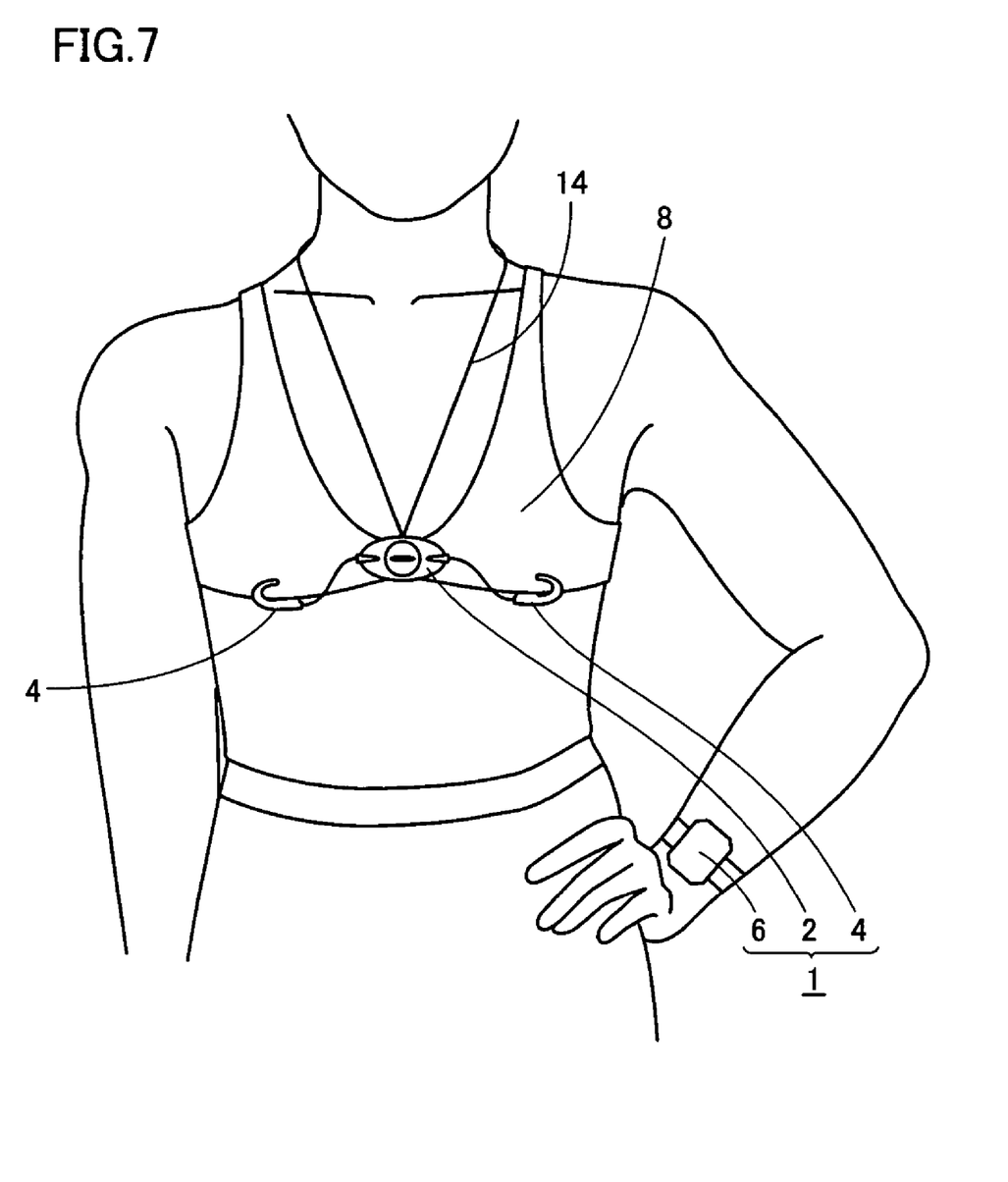
FIG. 7 is a front view illustrating the heartbeat detection device of the first embodiment shown in FIGS. 1 and 2 in the state of being mounted on the body.

Thus, when a subject wears such a sports brassiere 8 as shown in FIG. 7, a bottom part of sports brassiere 8 is sandwiched between electrode bodies 4a and hooks 4b of respective electrode units 4 while an upper part of sports brassiere 8 is sandwiched between transmitting-unit body 2a and hook 2b so that electrode units 4 and transmitting unit 2 are held on sports brassiere 8 without making the subject feel tight.

Moreover, transmitting unit 2 and electrode units 4 each are connected by respective wires, and accordingly transmitting unit 2 and electrode units 4 are separated from each other. Therefore, even if transmitting unit 2, which is relatively heavier than transmitting units 4, moves while the subject is doing some sport, the electrode units 4 do not follow the movement of transmitting unit 2. Contact of paired electrode units 4 with respective predetermined positions on the chest can thus be ensured, and accordingly a potential difference can be detected accurately. The detected potential difference is provided to transmitting unit 2 and then transmitted as a signal concerning heartbeat to receiving unit 6 mounted for example on the arm.

Further, since there is no need to provide paired electrode units 4 and transmitting unit 2 within one casing, the weight of heartbeat detection device 1 can be reduced.

It is noted that, the above-described heartbeat detection device may have a cord 14 of an appropriate length that is suspended from the neck and caught in hook 2b for the purpose of preventing transmitting unit 2, which is relatively heavier than electrode units 4, from being disengaged from sports brassiere 8 to drop therefrom as the subject moves.

Second Embodiment

The first embodiment has been described as being directed to an example of the heartbeat detection device having the electrode units and the transmitting unit directly held on a garment worn by a subject. The second embodiment is now described as being directed to an example thereof having the electrode units and the transmitting unit held on a predetermined attachment belt that is then mounted on the body of a subject.

Figure 8:
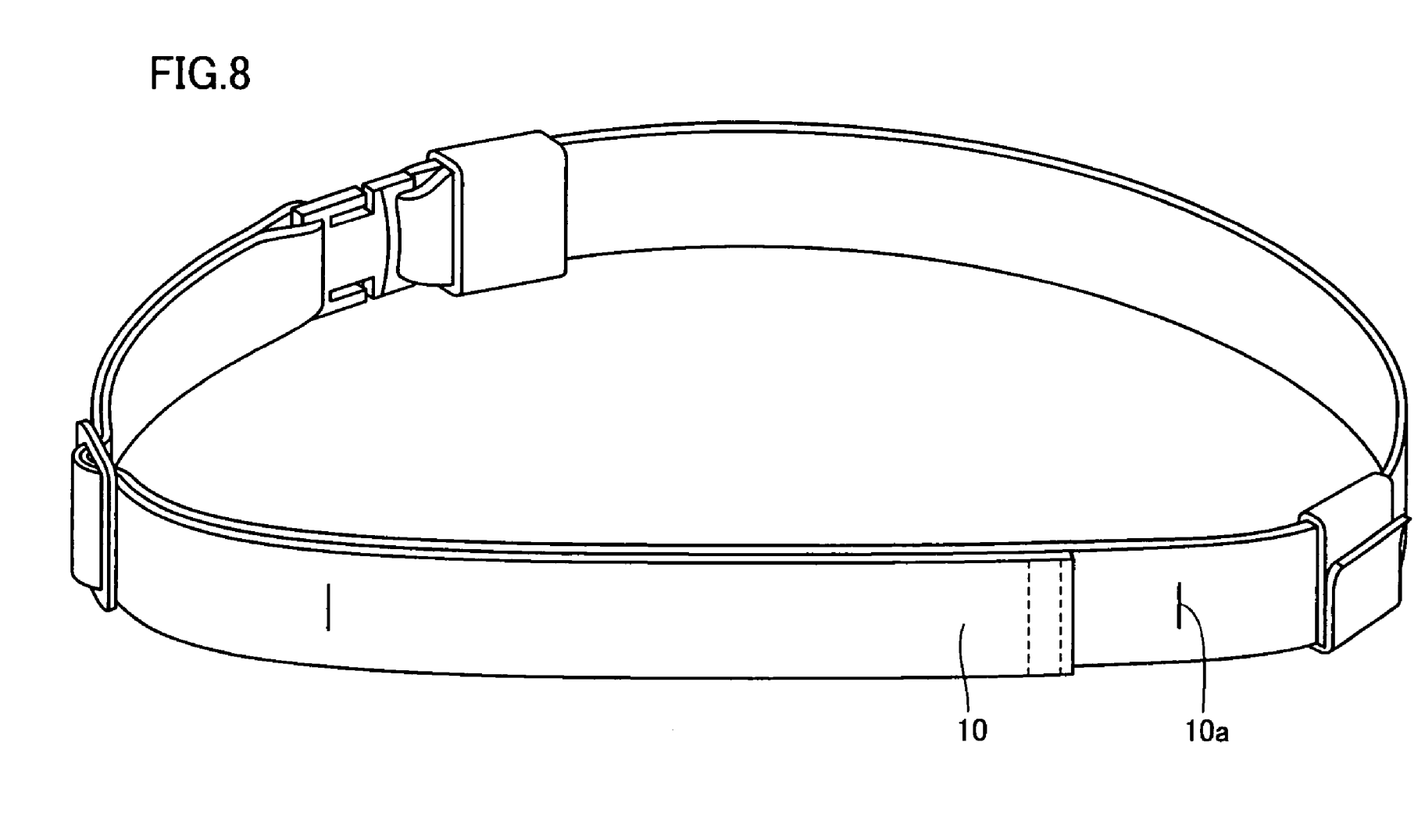
FIG. 8 is a perspective view illustrating an attachment belt of a heartbeat detection device according to a second embodiment of the present invention.
Figure 9:
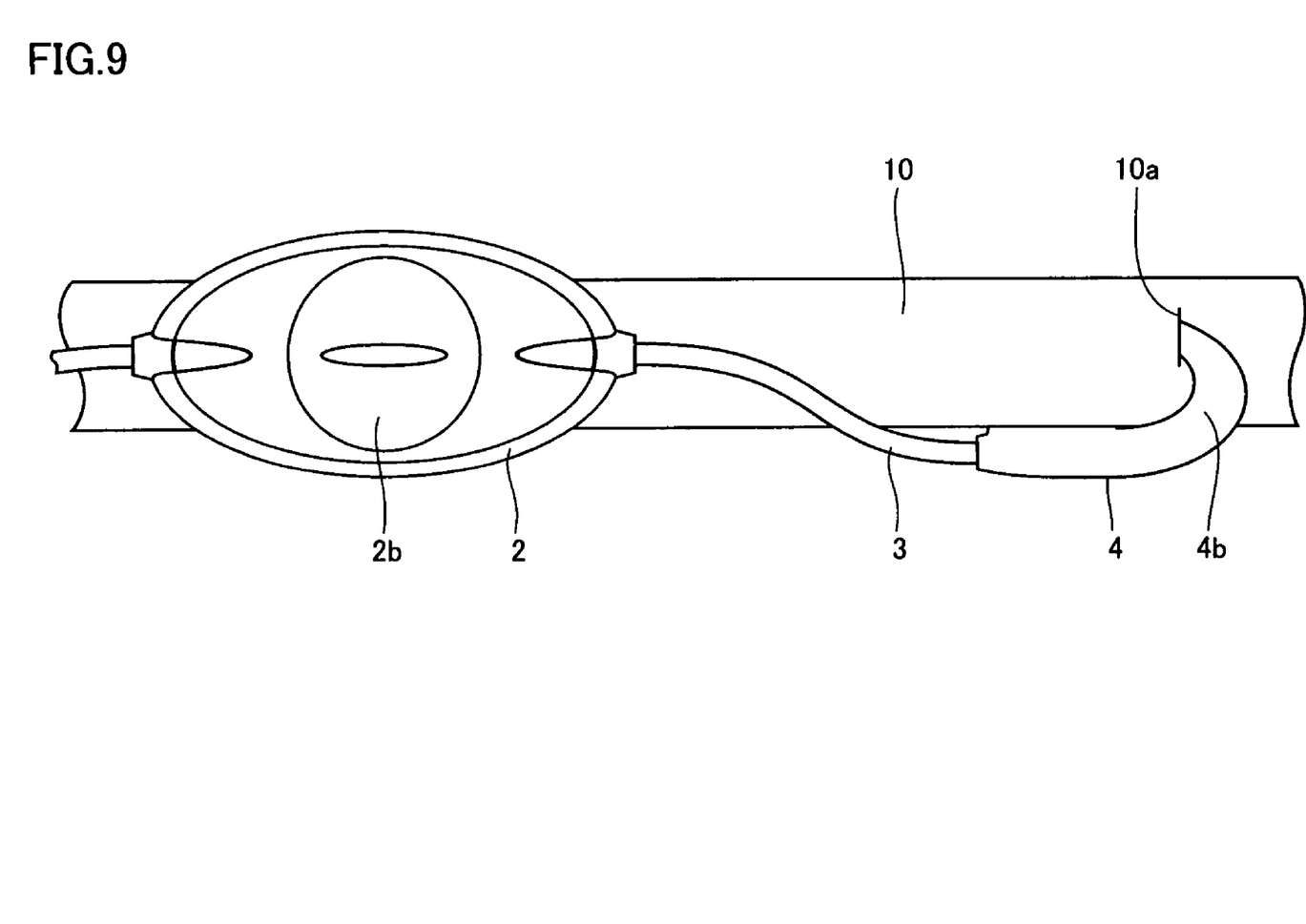
FIG. 9 is a partial front view showing the attachment belt in FIG. 8 of the second embodiment with the heartbeat detection device held on the belt.

Referring to FIG. 8, an attachment belt 10 has a cut 10a receiving hook 4b of electrode unit 4. Electrode unit 4 is attached to belt 10, as shown in FIG. 9, by sandwiching a bottom part of attachment belt 10 between electrode body 4a and hook 4b while inserting hook 4b into cut 10a.

Figure 10:
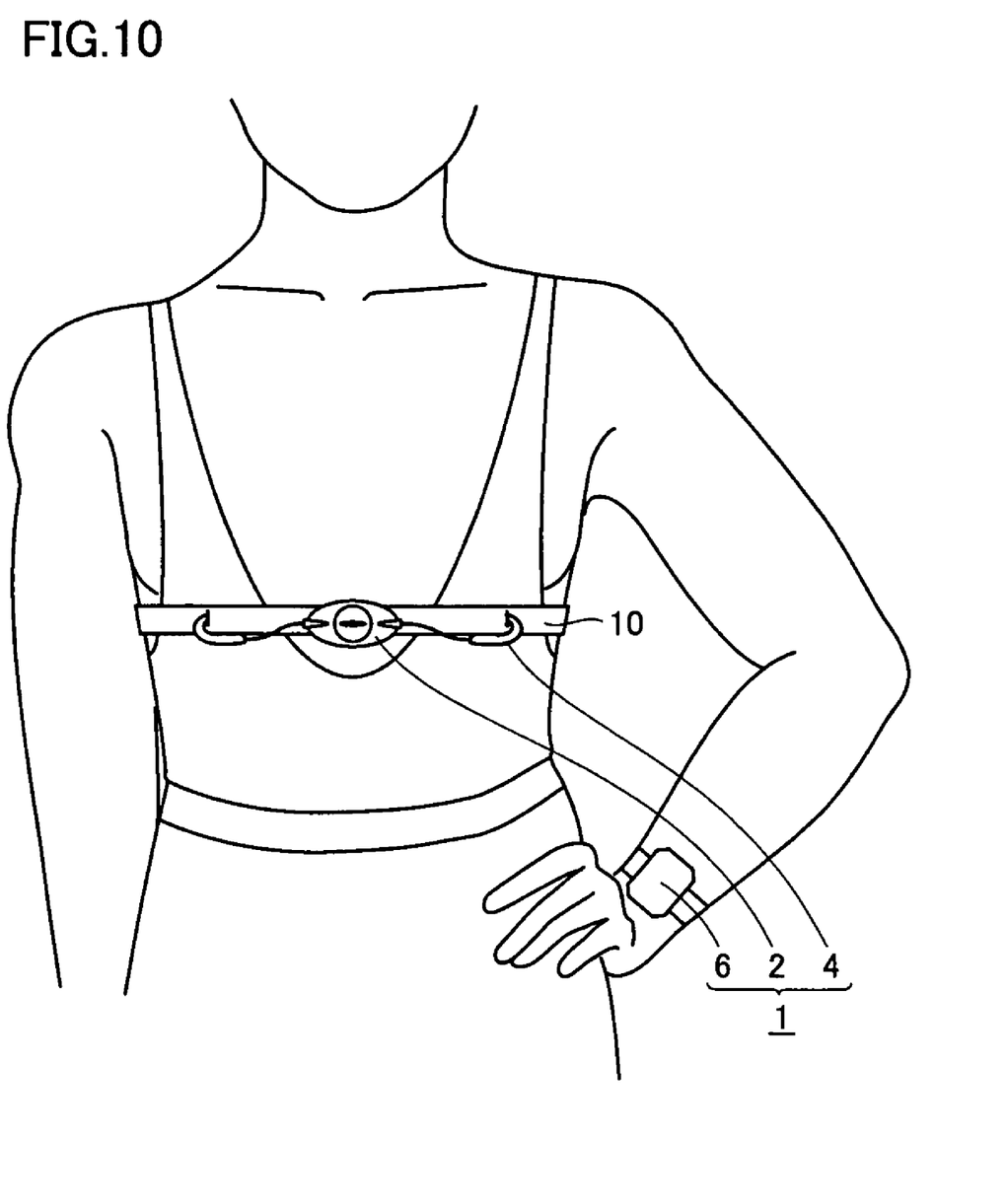
FIG. 10 is a front view illustrating the heartbeat detection device of the second embodiment shown in FIG. 9 in the state of being mounted on the body.

Transmitting unit 2 is attached to belt 10, by sandwiching an upper part of attachment belt 10 between transmitting-unit body 2a and hook 2b as described in connection with the first embodiment. In this way, paired electrode units 4 and transmitting unit 2 are attached to attachment belt 10 which is then wound around the chest so that paired electrode units 4 can be held on respective predetermined parts of the body as shown in FIG. 10.

Of the above-described heartbeat detection device, paired electrode units 4 and transmitting unit 2 are held on attachment belt 10 instead of being directly held on a garment, and attachment belt 10 is then wound around the chest. Accordingly, as compared with the case where a casing having a pair of electrode units and a transmitting unit provided therein is integrated into a belt which is then tightened around the chest, paired electrode units 4 of the present invention can surely be held at respective predetermined positions of the body of the subject with reduced feeling of tightness or pressure.

While direct contact between paired electrode units 4 and the body of a subject is preferable for the purpose of detecting the potential of the body, it is preferable, if there is such clothing as sports brassiere or sports shirt between electrode units 4 and the body (skin), to wet in advance certain parts of the body that are to be in contact with electrode units 4 for providing electrical conductance therebetween.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A heartbeat detection device comprising:
   a pair of electrode units for electrically contacting a body of a user proximate the chest for detecting an electric potential concerning heartbeat;
   a first clipping means provided each electrode unit of electrode units for retention on an article worn by the body for holding said pair of electrode units in close proximity to the chest of the body;
   a transmitting unit for transmitting, as a heartbeat signal, information about the electric potential detected by said pair of electrode units;
   said pair of electrode units and said transmitting unit being separate components;
   wire means connecting each of said pair of electrode units with said transmitting unit; said wire means comprising a first wire and a second wire, the first wire extending from one side of the transmitting unit and connected to one of the pair of electrode units and the second wire extending from another side of the transmitting unit and connected to the other of the pair of electrode units;
   the pair of electrode units and the transmitting unit being disposed in separate casings, respectively, and the casings being supported by the first wire and the second wire, respectively; and
   a receiving unit receiving the heartbeat signal transmitted from said transmitting unit.

2. The heartbeat detection device according to claim 1, wherein said pair of electrode units each include:
   an electrode body electrically contacting the chest of the body;
   a hook provided on a side of the electrode unit that is opposite to a side thereof which faces the body and on which said electrode body is provided; and
   said electrode body and said hook serve as said first clipping means for clipping from underneath the article worn by the body.

3. The heartbeat detection device according to claim 2, including an attachment belt constructed and arranged to be secured to the body; and
   a hook-inserted portion provided in said attachment belt for receiving said hook of said first clipping means to catch said pair of electrode units each by said attachment belt; and wherein
   said transmitting unit includes a second clipping means for clipping from above the attachment belt worn by the body.

4. The heartbeat detection device according to claim 3, including a ring-shaped cord constructed and arranged to be suspended from neck of the user, said ring-shaped cord engaging with the second clipping means.

5. The heartbeat detection device according to claim 2, further comprising:
   an attachment belt constructed and arranged to be secured to the body; and
   a hook-inserted portion provided in said attachment belt for receiving said hook of said first clipping means to catch said pair of electrode units each by said attachment belt.

6. The heartbeat detection device according to claim 1, wherein said pair of electrode units each include projections provided on a side of the electrode unit that faces the body.

* * * * *

UNITED STATES PATENT AND TRADEMARK OFFICE
CERTIFICATE OF CORRECTION

PATENT NO. : 7,330,751 B2 Page 1 of 1
APPLICATION NO. : 10/918886
DATED : February 12, 2008
INVENTOR(S) : Takashi Ueda It is certified that error appears in the above-identified patent and that said Letters Patent is hereby corrected as shown below:

Claim 1, line 5 (col. 5, line 54), please add -- to -- after "provided";

Claim 1, lines 5 and 6 (col. 5, lines 54 and 55), please delete "of electrode units"

Signed and Sealed this

First Day of July, 2008

JON W. DUDAS
*Director of the United States Patent and Trademark Office*